Jan. 16, 1968 F. W. ANDERSON Plant Pat. 2,789
APRICOT TREE
Filed Sept. 23, 1966
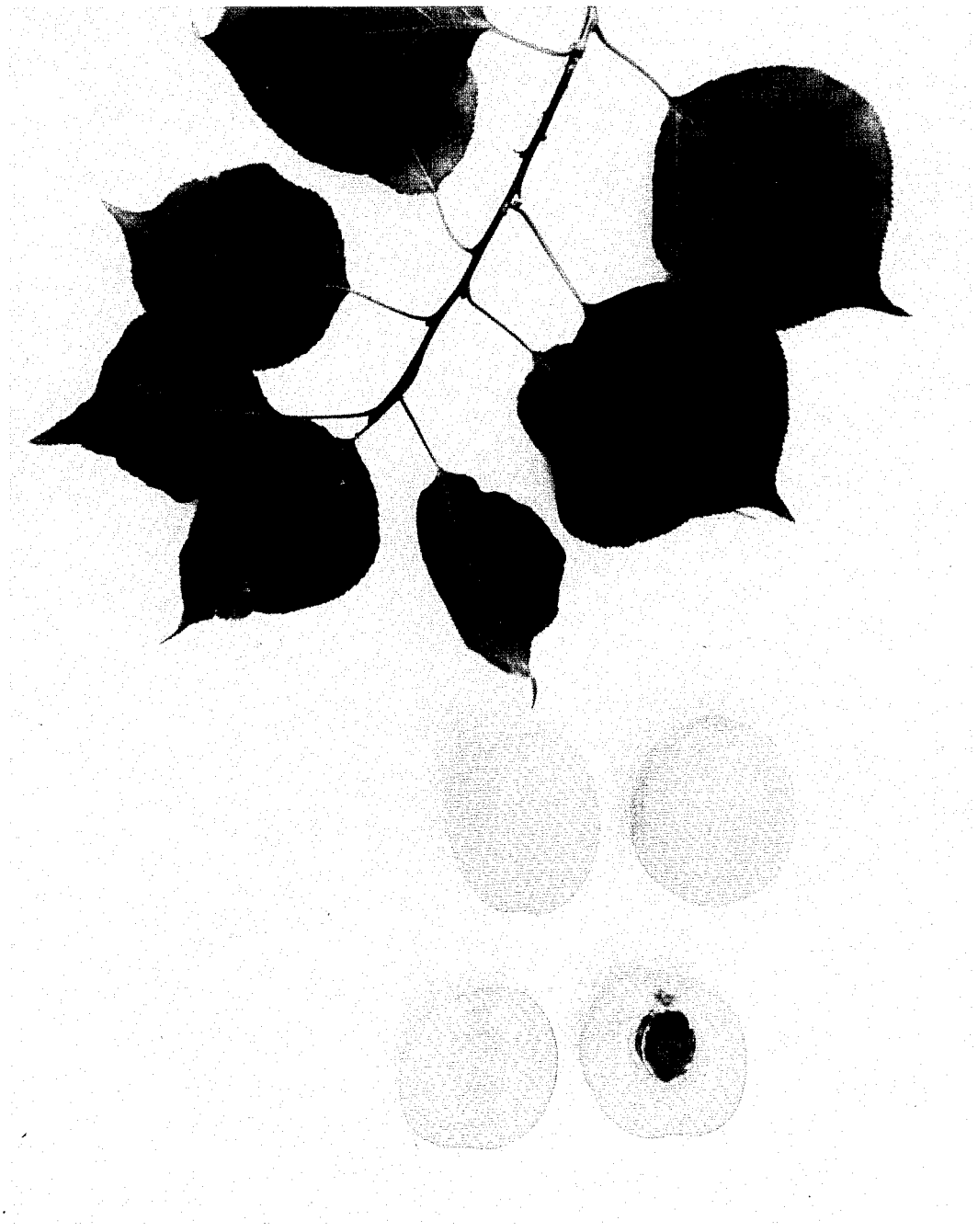
INVENTOR
Frederic W. Anderson
BY
Webster & Webster
ATTORNEYS

United States Patent Office

Plant Pat. 2,789

Patented Jan. 16, 1968

2,789

APRICOT TREE

Frederic W. Anderson, Merced, Calif., assignor, by mesne assignments, to Reedley Nursery, Inc., Reedley, Calif.

Filed Sept. 23, 1966, Ser. No. 581,665

1 Claim. (Cl. Plt.—39)

The present invention relates to a new and distinct variety of apricot tree which is characterized by the regular and productive bearing of early ripening, firm yellow flesh, freestone fruit; the fruit ripening approximately two weeks before the Royal apricot (unpatented), and about one week before the Pomo apricot (United States Plant Patent No. 2,192).

The herein claimed variety of apricot tree was originated by me as a second generation seedling of a Perfection apricot × Blenheim apricot; both the Perfection and Blenheim being unpatented. Such origination of the instant variety was accomplished by me, under conditions of close observation, in my experimental orchard located near Le Grand, Merced County, Calif.

Subsequent to origination of the present variety of apricot tree, and recognition by me of its novel and distinct characteristics, I asexually reproduced it by topworking on orchard trees in my experimental orchard located as aforesaid. When they came into bearing, all of such reproductions ran true in all respects to the original tree of the present variety.

The drawing comprises an illustration, by photographic reproduction in color, of a twig with leaves, two whole fruit, and another fruit cut in half to expose the flesh and with the stone remaining in one half.

Referring now more specifically to the promological details of this new and distinct variety of apricot tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Red to brown.
- *Lenticels.*—Number—medium. Size—medium.

Leaves:
- *Size.*—Medium. Average length—3". Average width—2¾".
- *Form.*—Acutely pointed.
- *Thickness.*—Medium.
- *Texture.*—Smooth.
- *Margin.*—Crenate.
- *Petiole.*—Long to medium.
- *Glands.*—Average number—variable (1–5). Alternate; medium size; positioned on petiole.
- *Color.*—Top side—Medium green (23–L8). Under side—Lighter Green (22–J–6).

Flower buds:
- *Size.*—Medium.
- *Length.*—Medium.

Flowers:
- *Blooming period.*—Date of first bloom— Feb. 20, 1966. Date of full bloom—Mar. 2, 1966. Early to medium compared with other varieties.
- *Color.*—White.

Fruit:
- *Maturity when described.*—Eating ripe—June 7, 1966.
- *Date of first picking.*—May 27, 1966.
- *Date of last picking.*—June 7, 1966.
- *Size.*—Uniform; medium. Average diameter axially—2". Average transversely in suture plane—1⅝".
- *Form.*—Uniform; symmetrical; compressed laterally.
- *Suture.*—Distinct to deep; extends from base to apex.
- *Ventral surface.*—Rounded slightly.
- *Lips.*—Equal.
- *Cavity.*—Elongated in suture plane with suture showing on one side.
- *Base.*—Truncate.
- *Apex.*—Depressed.

Skin:
- *Thickness.*—Thick to medium.
- *Texture.*—Medium.
- *Tenacity.*—Tenacious to flesh.
- *Tendency to crack.*—Slight.
- *Down.*—Moderate; short.
- *Color.*—Normal Apricot (11–L–8).

Flesh:
- *Amygdalin.*—Wanting.
- *Juice.*—Moderate.
- *Texture.*—Firm; meaty.
- *Fibers.*—Few.
- *Ripens.*—Evenly.
- *Flavor.*—Acid to subacid.
- *Aroma.*—Distinct.
- *Eating quality.*—Good.
- *Color.*—Normal Apricot (11–L–8).

Stone:
- *Type.*—Free.
- *Size.*—Medium. Average length—1". Average breadth—¾". Average thickness—½".
- *Form.*—Ovoid.
- *Base.*—Straight.
- *Apex.*—Rounded.
- *Sides.*—Equal.
- *Tendency to split.*—None.
- *Kernel.*—Bitter.
- *Color.*—Medium Brown (8–H–11).

Use: Market; Dessert.
Keeping quality: Good.
Shipping quality: Good—by reason of firm flesh.

The tree and its fruit herein described may vary in slight detail due to climatic and soil conditions under which the variety may be grown; the present description being of the variety as grown in the Central Valley of California.

The following is claimed:

1. A new and distinct variety of apricot tree, substantially as illustrated and described, characterized by the regular and productive bearing of early ripening, firm yellow flesh, freestone fruit; the fruit ripening approximately two weeks before the Royal apricot, and about one week before the Pomo apricot.

No references cited.

ROBERT E. BAGWILL, *Primary Examiner.*